United States Patent
Ono

(10) Patent No.: US 8,866,893 B2
(45) Date of Patent: Oct. 21, 2014

(54) IMAGING APPARATUS

(71) Applicant: Olympus Medical Systems Corp., Tokyo (JP)

(72) Inventor: Wataru Ono, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/873,305

(22) Filed: Apr. 30, 2013

(65) Prior Publication Data

US 2013/0300849 A1   Nov. 14, 2013

Related U.S. Application Data

(63) Continuation of application No. PCT/JP2012/083649, filed on Dec. 26, 2012.

(30) Foreign Application Priority Data

Dec. 27, 2011   (JP) .................... 2011-285333

(51) Int. Cl.

| A61B 1/04 | (2006.01) |
| A61B 1/06 | (2006.01) |
| A61B 1/00 | (2006.01) |
| A61B 1/05 | (2006.01) |
| H04N 7/18 | (2006.01) |

(52) U.S. Cl.
CPC .............. *H04N 7/18* (2013.01); *A61B 1/00006* (2013.01); *A61B 1/051* (2013.01); *A61B 1/0638* (2013.01)
USPC .......................................... 348/68

(58) Field of Classification Search
CPC . G02B 27/025; G02B 27/027; A61B 1/00193
USPC .......................................... 348/68
See application file for complete search history.

(56) References Cited

U.S. PATENT DOCUMENTS

| 2009/0080175 A1 | 3/2009 | Mizuno et al. |
| 2010/0069713 A1 | 3/2010 | Endo et al. |

FOREIGN PATENT DOCUMENTS

| JP | 2003-116784 A | 4/2003 |
| JP | 2004-57420 A | 2/2004 |

(Continued)

OTHER PUBLICATIONS

International Search Report from related PCT/JP2012/083649, dated Jan. 29, 2013.

(Continued)

*Primary Examiner* — Mehrdad Dastouri
*Assistant Examiner* — Kristin Dobbs
(74) *Attorney, Agent, or Firm* — Scully, Scott, Murphy & Presser, PC

(57) ABSTRACT

Imaging apparatus performs controlling to read pixel information from pixels belonging to target area by each frame. One frame period is period from when an exposure period for exposing pixels on a horizontal line that is to be read first from among horizontal lines belonging to the target area of a sensor is started and until when reading of the pixel information generated by each of the pixels on the horizontal line is completed. The imaging apparatus sequentially emits, by each illumination period of a length corresponding to at least two frame periods, illumination lights in synchronization with start of the exposure period. The imaging apparatus performs a predetermined controlling by performing controlling to exclude, from predetermined processing target, image data corresponding to the pixel information read during first frame period of the illumination period, while by acquiring image data corresponding to the pixel information read during other frame period.

5 Claims, 12 Drawing Sheets

(56) References Cited

FOREIGN PATENT DOCUMENTS

| | | |
|---|---|---|
| JP | 2006-280465 A | 10/2006 |
| JP | 2010-68992 A | 4/2010 |
| JP | 2011-206336 A | 10/2011 |
| JP | 2011-206338 A | 10/2011 |
| JP | 2011-211553 A | 10/2011 |
| JP | 2011-235021 A | 11/2011 |
| JP | 2011-250926 A | 12/2011 |

OTHER PUBLICATIONS

Notice of Rejection dated Jul. 16, 2013 from corresponding Japanese Patent Application No. 2013-519890, together with a partial English language translation.

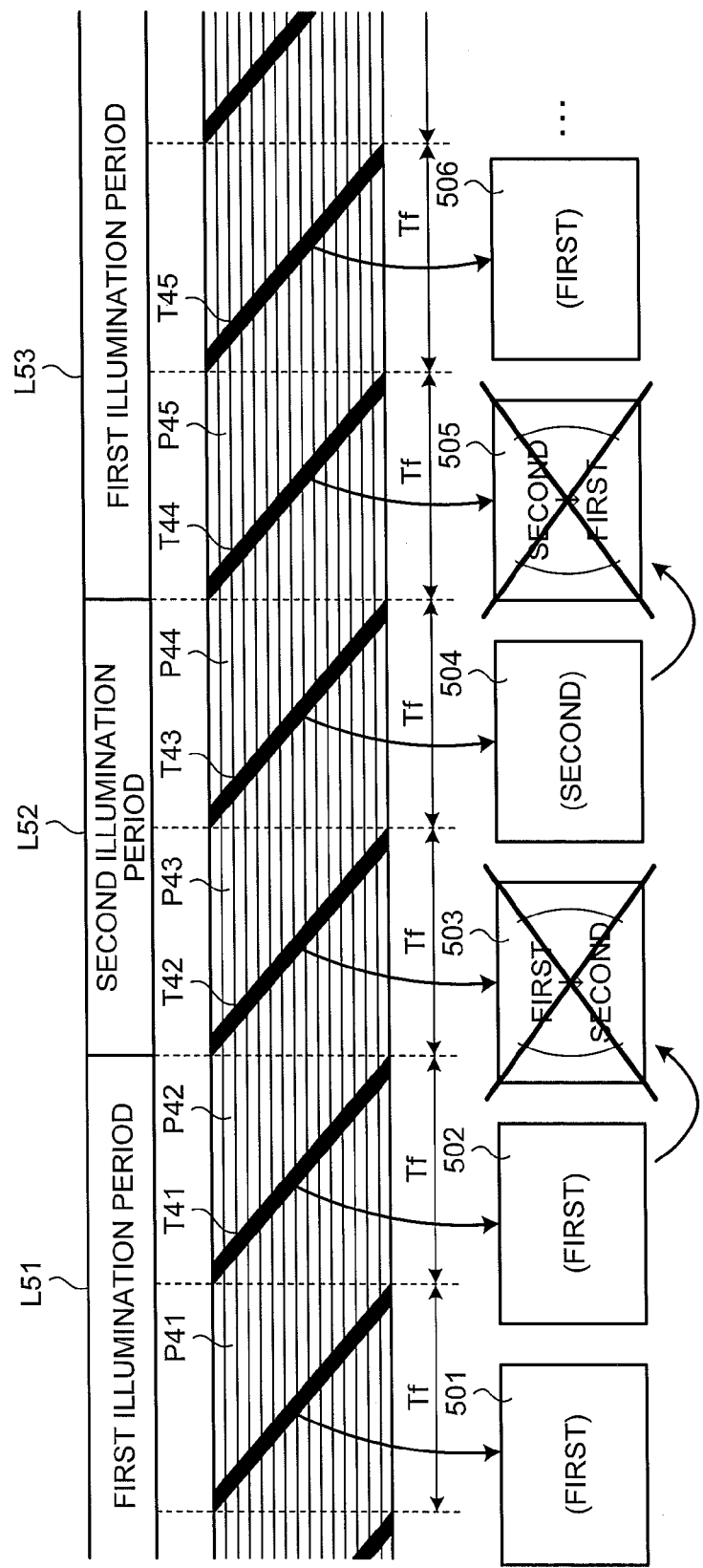

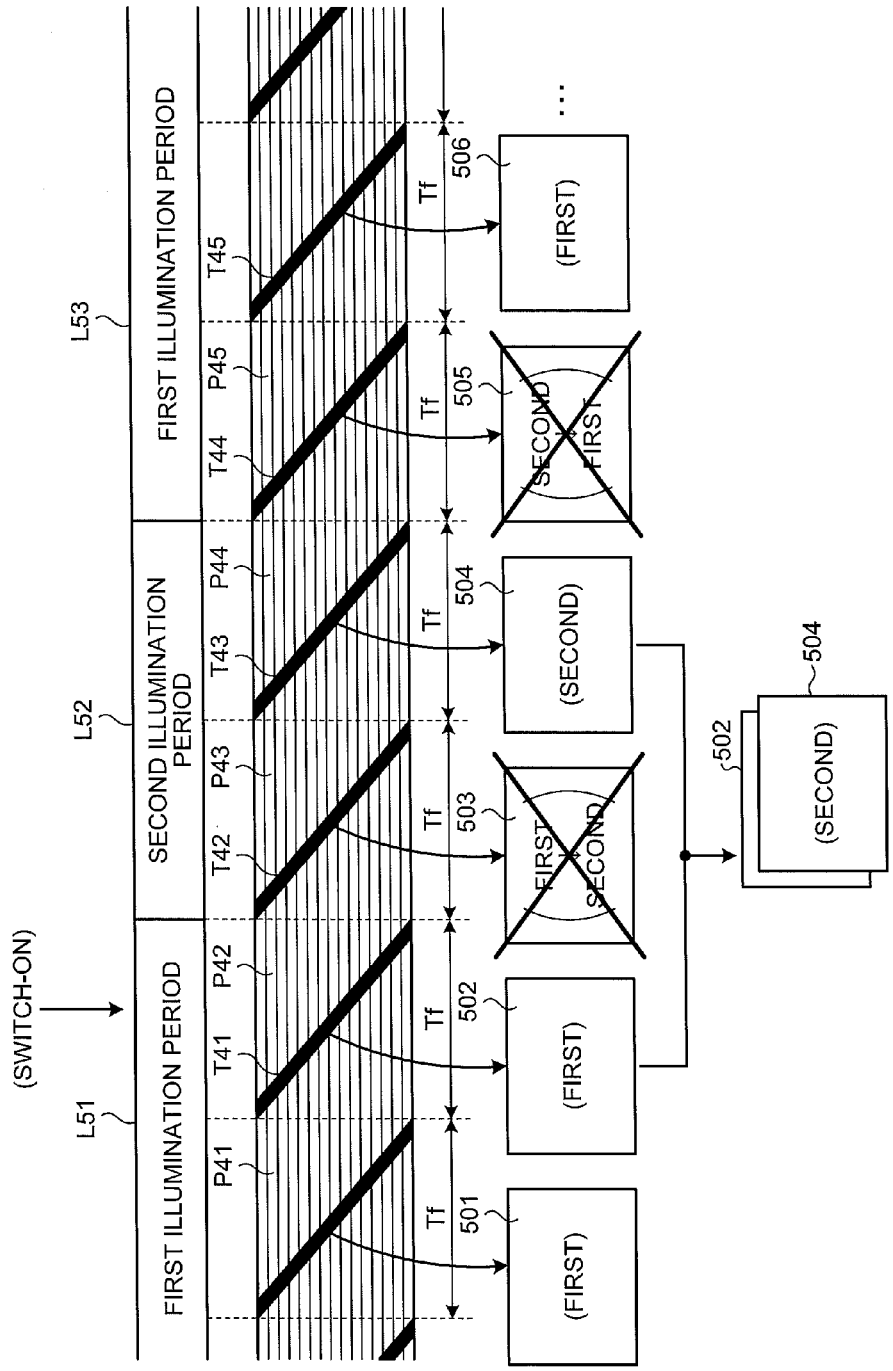

IMAGING APPARATUS

CROSS REFERENCES TO RELATED APPLICATIONS

This application is a continuation of PCT international application Ser. No. PCT/JP2012/083649 filed on Dec. 26, 2012 which designates the United States, incorporated herein by reference, and which claims the benefit of priority from Japanese Patent Applications No. 2011-285333, filed on Dec. 27, 2011, incorporated herein by reference.

BACKGROUND OF THE INVENTION

1. Field of the Invention

The present invention relates to an imaging apparatus including an imaging element that can output, as pixel information, a photoelectrically-converted electrical signal from a pixel arbitrarily designated as a target to be read from among a plurality of pixels for imaging.

2. Description of the Related Art

Conventionally, in the field of medicine, an endoscope system is used to observe an organ of a subject, such as a patient. The endoscope system includes: an insertion portion that is in an elongated flexible shape and to be inserted into a body cavity of a subject; an imaging unit that is arranged at a distal end of the insertion portion and captures an in-vivo image; and a display unit that can display the in-vivo image captured by the imaging unit. To capture an in-vivo image by using the endoscope system, the insertion portion is inserted into a body cavity of a subject, and thereafter, illumination light, such as white light, is irradiated to body tissues in the body cavity from the distal end of the insertion portion and the imaging unit captures an in-vivo image. A user, such as a doctor, observes an organ of the subject based on the in-vivo image displayed by the display unit.

To perform observation by using the endoscope system, in some cases, a plurality of types of illuminations are switched at predetermined timings. As such method of illumination, for example, a frame sequential method is known in which a plurality of types of illumination lights for three color components of red (R), green (G), and blue (B) are sequentially switched (see, for example, Japanese Laid-open Patent Publication No. 2006-280465). In this technology, images are individually captured under sequentially-switched illumination light by using a CCD (Charge Coupled Device) image sensor.

SUMMARY OF THE INVENTION

An imaging apparatus according to a present invention includes: a light source unit; a sensor; a control unit; and a light source controller. The light source unit is capable of emitting a plurality of types of illumination lights. In the sensor, a plurality of pixels that each generates, upon receipt of light, an electrical signal through photoelectric conversion are arranged on a two-dimensional plane. The sensor is capable of reading, as pixel information, electrical signals generated by pixels arbitrary designated as a read target area from among the pixels, and is capable of sequentially reading a plurality of horizontal lines on a line-by-line basis. The control unit performs controlling to read the pixel information from the pixels belonging to the read target area by each frame. One frame period is a period from when an exposure period for exposing the pixels on a horizontal line that is to be read first from among the horizontal lines belonging to the read target area of the sensor is started and until when reading of the pixel information generated by each of the pixels on the horizontal line is completed. The light source controller controls the light source unit to sequentially emit, by each illumination period of a length corresponding to at least two frame periods, the illumination lights in synchronization with start of the exposure period of the horizontal line that is to be read first from the sensor. The control unit performs the predetermined controlling by performing controlling to exclude, from a predetermined processing target, image data corresponding to the pixel information read by the sensor during a first frame period of the illumination period among the pixel information read by the sensor in each frame, while on the other hand by acquiring image data corresponding to the pixel information read by the sensor during other frame period of the illumination period among the pixel information read by the sensor in each frame.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 11 is a diagram schematically illustrating an overview of an image acquiring method characteristic for an endoscope system according to Embodiment 3 of the present invention; and FIG. 12 is a diagram schematically illustrating an overview of an image acquiring method characteristic for an endoscope system according to Modification 3-1 of Embodiment 3 of the present invention.

DETAILED DESCRIPTION OF THE PREFERRED EMBODIMENTS

Exemplary embodiments (hereinafter, described as "embodiments") of the present invention will be explained below with reference to the accompanying drawings. The drawings referred to in the following description are schematic and different drawings may illustrate the same object with different dimensions and different scales.

Embodiment 1

Figure 1:
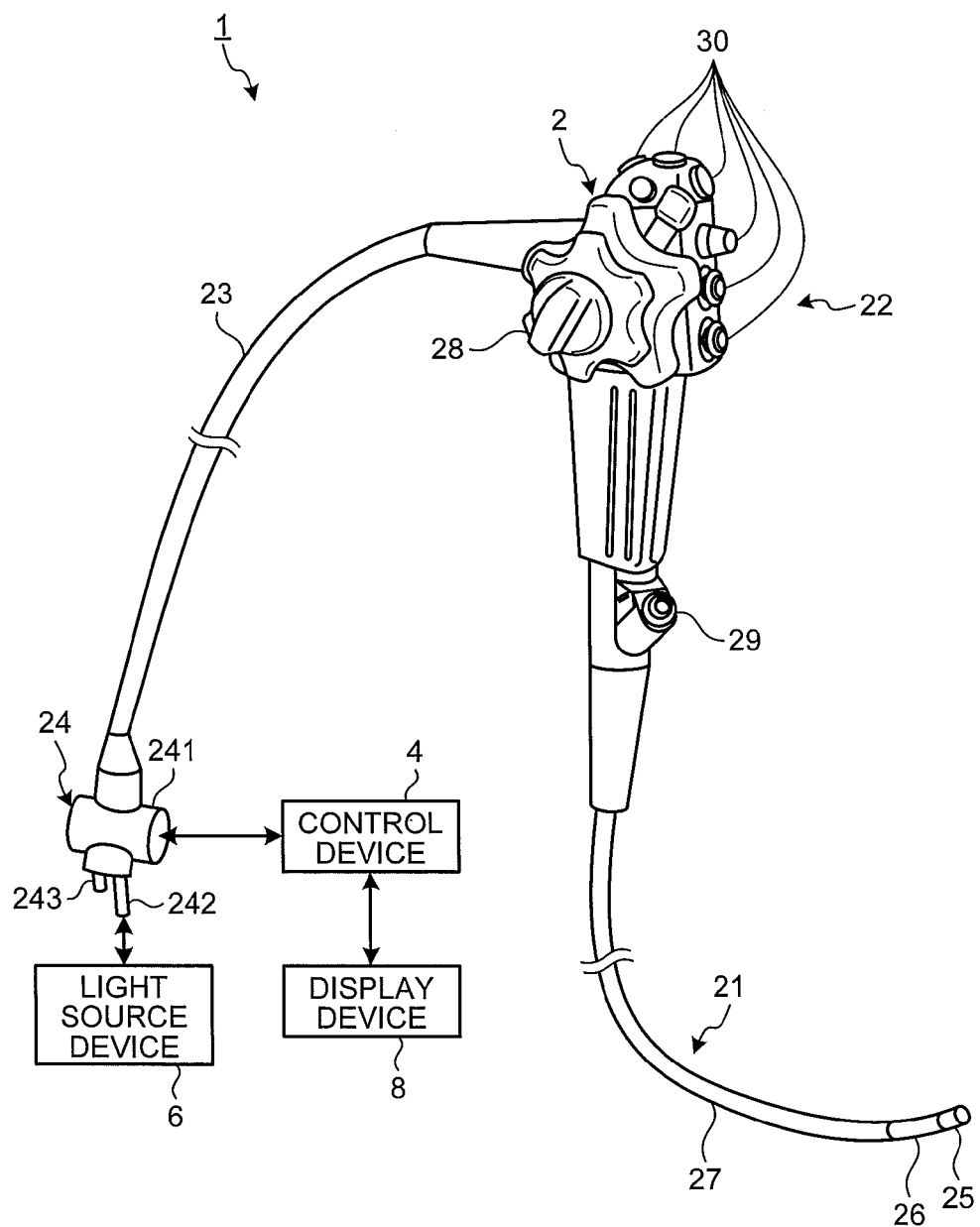
FIG. 1 is a diagram illustrating a schematic configuration of an endoscope system serving as an imaging apparatus according to Embodiment 1 of the present invention.

FIG. 1 is a diagram illustrating a schematic configuration of an endoscope system serving as an imaging apparatus according to Embodiment 1 of the present invention. An endoscope system 1 illustrated in FIG. 1 includes: an endoscope 2 that captures an in-vivo image of a subject by inserting a tip portion into a body cavity of the subject; a control device 4 that has a function to perform processing on the in-vivo image acquired by the endoscope 2 and a function to integrally control the entire operation of the endoscope system 1; a light source device 6 that generates illumination light to be emitted from a distal end of the endoscope 2; and a display device 8 that displays the in-vivo image subjected to image processing by the control device 4.

The endoscope 2 includes: an elongated flexible insertion portion 21; an operation unit 22 that is connected to the proximal end of the insertion portion 21 and that receives input of an operation signal; a universal code 23 that extends in a direction different from a direction in which the insertion portion 21 extends from the operation unit 22 and that includes various built-in cables connected to the control device 4 and the light source device 6; and a connector 24 that is disposed at a tip portion of the universal code 23 and that establishes connections among the endoscope 2, the control device 4, and the light source device 6.

The insertion portion 21 includes: a tip portion 25 in which an imaging element to be described later is provided; a curved portion 26 that includes a plurality of curved pieces and that can be curved; and a flexible tube 27 that is connected to the proximal end of the curved portion 26 and that is long and flexible.

Figure 2:
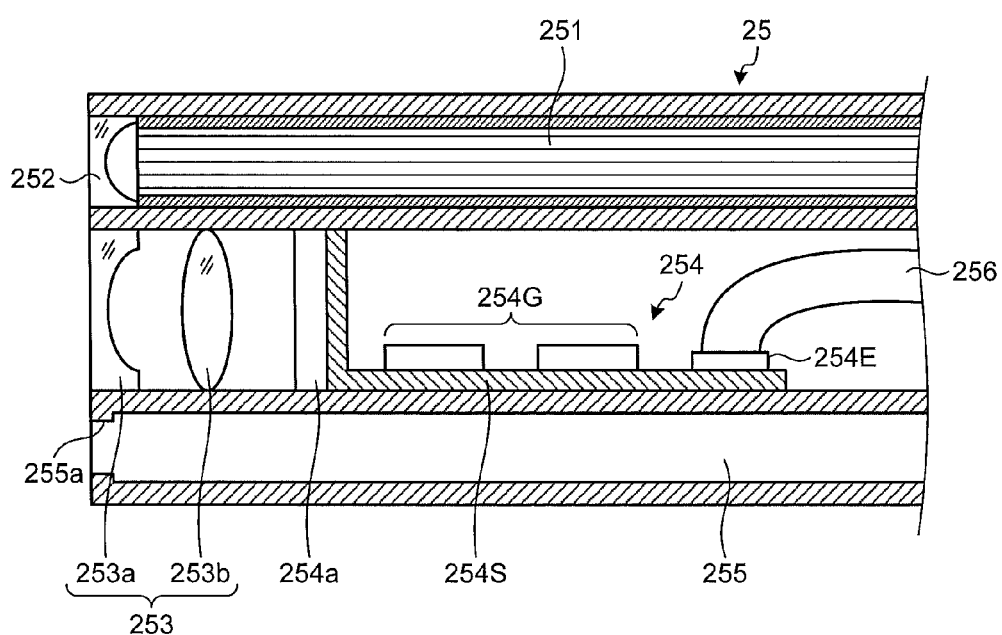
FIG. 2 is a cross-sectional view schematically illustrating an internal configuration of a tip portion of an endoscope included in the endoscope system according to Embodiment 1 of the present invention.

FIG. 2 is a cross-sectional view schematically illustrating an internal configuration of the tip portion 25. As illustrated in FIG. 2, the tip portion 25 includes: a light guide 251 that is formed using glass fibers or the like and serves as a light guide for light generated by the light source device 6; an illumination lens 252 disposed at an end of the light guide 251; an optical system 253 for collecting light; an imaging element 254 that is disposed at an imaging position of the optical system 253, receives light collected by the optical system 253, performs photoelectric conversion to obtain an electrical signal, and performs predetermined signal processing; and a treatment tool channel 255 for inserting a treatment tool for the endoscope 2.

The optical system 253 includes two lenses 253a and 253b. The types and number of the lenses included in the optical system 253 are not limited to those illustrated in FIG. 2.

Figure 3:
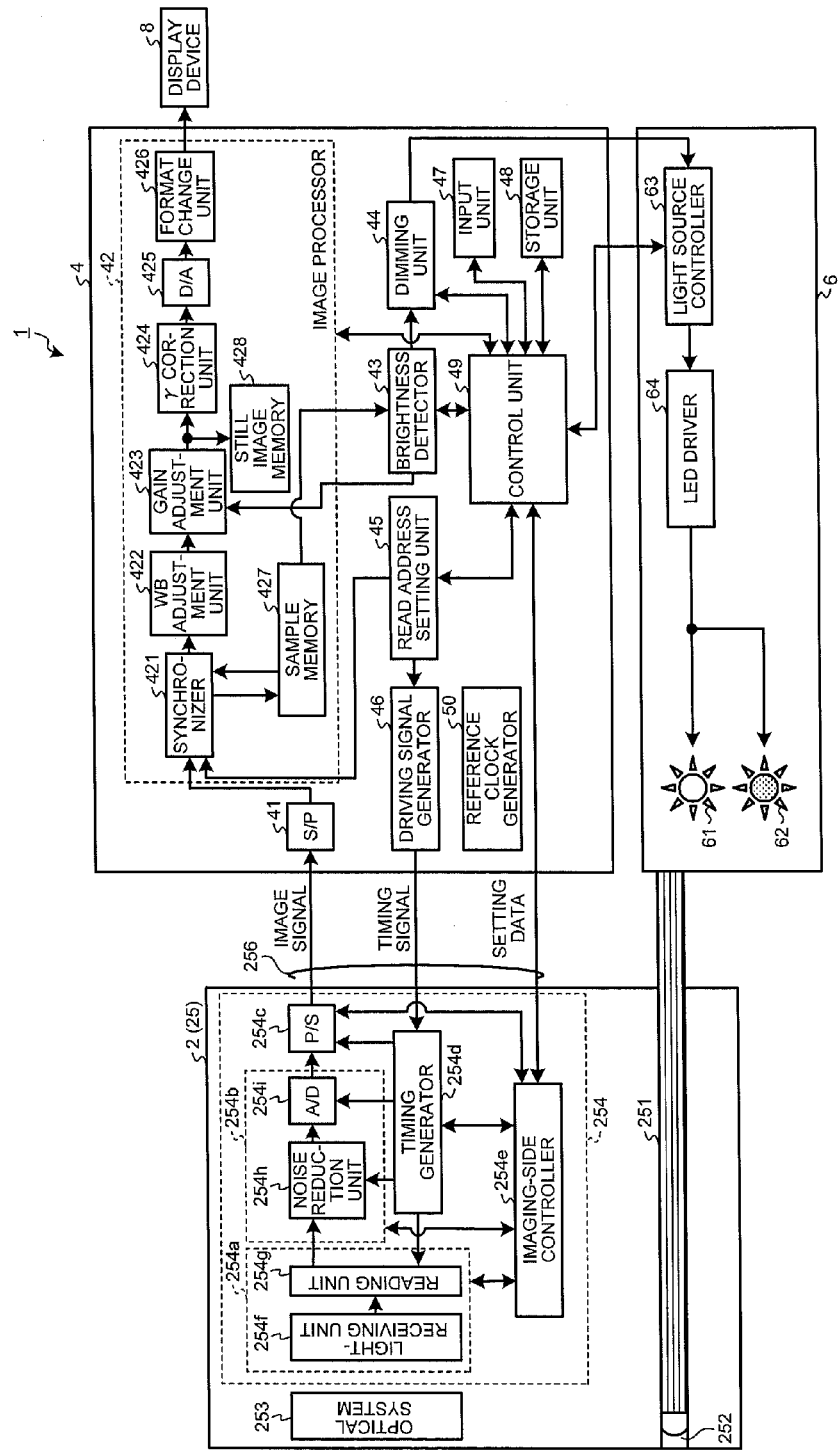
FIG. 3 is a block diagram illustrating a functional configuration of a main part of the endoscope system according to Embodiment 1 of the present invention.

FIG. 3 is a block diagram illustrating a functional configuration of a main part of the endoscope system 1. A configuration of the imaging element 254 will be explained with reference to FIG. 3. The imaging element 254 includes: a sensor 254a that performs photoelectric conversion on light received from the optical system 253 and outputs an electrical signal; an analog front end (AFE) unit 254b that performs noise elimination or A/D conversion on the electrical signal output by the sensor 254a; a P/S converter 254c that performs parallel-to-serial conversion on a digital signal output by the analog front end unit 254b; a timing generator 254d that generates a timing pulse for driving the sensor 254a and a pulse for various types of signal processing performed by the analog front end unit 254b and the P/S converter 254c; and an imaging-side controller 254e that controls operations of the imaging element 254. The imaging element 254 is a CMOS (Complementary Metal Oxide Semiconductor) image sensor.

The sensor 254a is connected to an IC circuit group 254G via a substrate 254S. The IC circuit group 254G includes a plurality of IC circuits having functions of the analog front end unit 254b, the P/S converter 254c, the timing generator 254d, and the imaging-side controller 254e.

The sensor 254a includes: a light-receiving unit 254f in which a plurality of pixels are disposed in a two dimensional matrix manner; and a reading unit 254g that reads, as pixel information, electrical signals generated by some of the pixels of the light-receiving unit 254f arbitrarily designated as targets to be read. Here, each of the pixels includes a photodiode for accumulating charges corresponding to the light intensity and an amplifier for amplifying the charges accumulated by the photodiode. Any of individual RGB color filters is provided at each of the pixels of the light-receiving unit 254f so that a color image can be acquired.

The analog front end unit 254b includes a noise reduction unit 254h that reduces noise components contained in a signal, and an A/D converter 254i that performs A/D conversion on the signal in which noise is reduced. The noise reduction unit 254h reduces noise by using, for example, correlated double sampling (Correlated Double Sampling) method. An AGC (Auto Gain Control) circuit that automatically adjusts a signal gain to constantly maintain a certain output level may be disposed between the noise reduction unit 254h and the A/D converter 254i.

The imaging-side controller 254e controls various operations of the tip portion 25 according to designated data received from the control device 4. The imaging-side controller 254e includes a CPU (Central Processing Unit) or the like.

An assembly cable 256, in which a plurality of signal lines for transmitting and receiving electrical signals to and from the control device 4 are bundled, is connected to an electrode 254E provided on the substrate 254S. The signal lines include a signal line for transmitting an image signal output by the imaging element 254 to the control device 4, a signal line for transmitting a control signal output by the control device 4 to the imaging element 254, and the like.

The operation unit 22 includes: a bending knob 28 for bending the curved portion 26 in the vertical direction and the horizontal direction; a treatment tool insertion portion 29 for inserting a treatment tool, such as a biopsy forceps or a laser probe, into the body cavity; and a plurality of switches 30 serving as operation input units for inputting operation instruction signals of the control device 4, the light source device 6, and peripheral devices, such as an air supply means, a water supply means, and a gas supply means. A treatment tool inserted from the treatment tool insertion portion 29 gets out of an opening 255a through the treatment tool channel 255 of the tip portion 25.

In the universal code 23, at least the light guide 251 and the assembly cable 256 are built-in.

The connector 24 includes an electric contact portion 241 connected to the control device 4, a light guide connector 242 detachably connected to the light source device 6, and an air supply mouthpiece 243 for sending air to a nozzle of the tip portion 25.

Next, a configuration of the control device 4 will be explained. The control device 4 includes: an S/P converter 41; an image processor 42; a brightness detector 43; a dimming unit 44; a read address setting unit 45; a driving signal generator 46; an input unit 47; a storage unit 48; a control unit 49; and a reference clock generator 50.

The S/P converter 41 performs serial-to-parallel conversion on an image signal (digital signal) received from the tip portion 25.

The image processor 42 generates an in-vivo image displayed by the display device 8 based on a parallel image signal output by the S/P converter 41. The image processor 42 includes: a synchronizer 421; a white balance (WB) adjustment unit 422; a gain adjustment unit 423; a γ correction unit 424; a D/A converter 425; a format change unit 426; a sample memory 427; and a still image memory 428.

The synchronizer 421 inputs image signals received as pixel information into three memories (not illustrated) provided for each pixel, stores each memory value in association with addresses of the pixels of the light-receiving unit 254f read by the reading unit 254g while sequentially updating the memory values, and synchronizes the image signals of the three memories as RGB image signals. The synchronizer 421 sequentially outputs the synchronized RGB image signals to the white balance adjustment unit 422, and outputs some of the RGB image signals to the sample memory 427 for image analysis, such as brightness detection.

The white balance adjustment unit 422 adjusts white balance of the RGB image signals.

The gain adjustment unit 423 adjusts gains of the RGB image signals. The gain adjustment unit 423 outputs the RGB signals with the adjusted gains to the γ correction unit 424, and outputs some of the RGB signals to the still image memory 428 for still image display, enlarged image display, or weighted image display.

The γ correction unit 424 performs tone correction (γ correction) on the RGB image signals according to the display device 8.

The D/A converter 425 converts the tone-corrected RGB image signals output by the γ correction unit 424 into analog signals.

The format change unit 426 changes a format of the image signals converted to the analog signals to a file format for moving images, and outputs the signals to the display device 8. As the file format, an AVI format, an MPEG format, or the like may be used.

The brightness detector 43 detects a brightness level corresponding to each pixel from the RGB signals stored in the sample memory 427, records the detected brightness level in a built-in memory, and outputs the brightness level to the control unit 49. In addition, the brightness detector 43 calculates a gain adjustment value and the amount of light emission on the basis of the detected brightness level, outputs the gain adjustment value to the gain adjustment unit 423, and outputs the amount of light emission to the dimming unit 44.

The dimming unit 44 sets a type, an amount, and an emission timing of light generated by the light source device 6 on the basis of the amount of light emission calculated by the brightness detector 43 under the control of the control unit 49, and transmits a light-source synchronous signal including the set conditions to the light source device 6.

The read address setting unit 45 has a function to set read target pixels of the light-receiving unit of the sensor 254a and an order in which the pixels are read. Specifically, the read address setting unit 45 has a function to set addresses of the pixels of the sensor 254a to be read by the analog front end unit 254b. In addition, the read address setting unit 45 outputs information on the set addresses of the read target pixels to the synchronizer 421.

The driving signal generator 46 generates a driving timing signal for driving the imaging element 254, and transmits the driving timing signal to the timing generator 254d through a predetermined signal line included in the assembly cable 256. The timing signal contains address information on the read target pixels.

The input unit 47 receives input of various signals, such as an operation instruction signal to give an instruction on operations of the endoscope system 1.

The storage unit 48 is realized by a semiconductor memory, such as a flash memory or a DRAM (Dynamic Random Access Memory). The storage unit 48 stores therein various programs for operating the endoscope system 1 and data including various parameters needed to operate the endoscope system 1.

The control unit 49 includes a CPU or the like, controls driving of each of the units including the tip portion 25 and the light source device 6, and controls input and output of information with respect to each of the units. The control unit 49 transmits setting data for controlling imaging to the imaging-side controller 254e through a predetermined signal line included in the assembly cable 256. The setting data includes an imaging speed (frame rate) of the imaging element 254, instruction information for giving an instruction on the speed for reading pixel information from an arbitrary pixel of the sensor 254a, and transmission control information on the pixel information read by the analog front end unit 254b.

The reference clock generator 50 generates a reference clock signal, which is a standard for operations of each unit of the endoscope system 1, and supplies the generated reference clock signal to each unit of the endoscope system 1.

Next, a configuration of the light source device 6 will be explained. The light source device 6 is a device that can emit a plurality of types of illumination lights with different spectral characteristics. Specifically, the light source device 6 includes: a white light source 61; a special light source 62; a light source controller 63; and an LED (Light Emitting Diode) driver 64. The white light source 61 and the special light source 62 constitute a part of a light source unit.

The white light source 61 includes a white LED and emits white illumination light.

The special light source 62 generates, as special light, light of any of R, G, and B components, which is in a specific wavelength band different from the wavelength band of white illumination light and the bandwidth of which is narrowed by a narrowband bandpass filter. Examples of the special light generated by the special light source 62 include NBI (Narrow Band Imaging) illumination light in two different bandwidths for blue light and green light whose bandwidths are narrowed so as to be easily absorbed by hemoglobin in blood, and excitation light for producing fluorescence at a predetermined wavelength.

The light source controller 63 controls an amount of current supplied to the white light source 61 or the special light source 62 in accordance with the light-source synchronous signal transmitted from the dimming unit 44. More specifically, assuming that one frame period is a period from when an exposure period for exposing a plurality of pixels on a horizontal line that is to be read first from among a plurality of horizontal lines belonging to a read target area of the sensor 254a is started and until when reading the pixel information generated by each of the pixels on the horizontal line is completed, the light source controller 63 controls the light source unit to sequentially emit, by each illumination period of a length corresponding to at least two frame periods, a plurality of types of illumination lights in synchronization with the start of the exposure period of the horizontal line that is to be read first by the sensor 254a.

The LED driver 64 supplies electric current to the white light source 61 or the special light source 62 under the control of the light source controller 63, to thereby cause the white light source 61 or the special light source 62 to generate light.

The light generated by the white light source 61 or the special light source 62 is emitted to the outside from an end of the tip portion 25 through the light guide 251.

The display device 8 has a function to receive an in-vivo image generated by the control device 4 from the control device 4 and display the in-vivo image. The display device 8 includes a display, such as a liquid crystal display or an organic EL (Electro Luminescence) display.

Figure 4:
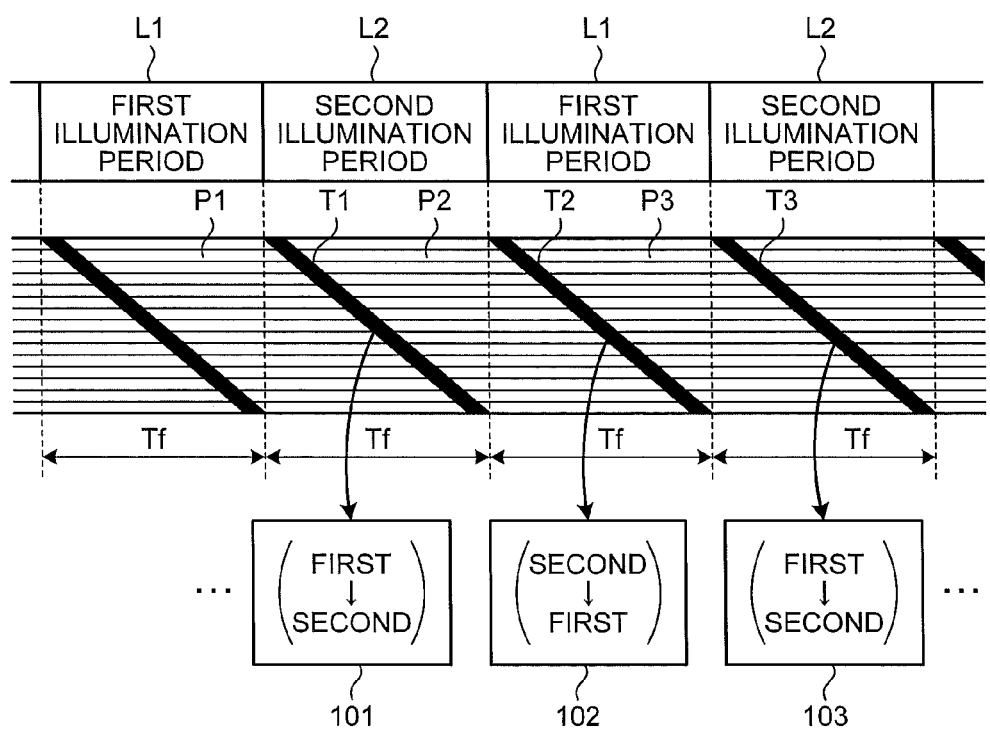
FIG. 4 is a diagram schematically illustrating an image acquiring method that can be performed by the endoscope system according to Embodiment 1 of the present invention.

FIG. 4 is a diagram schematically illustrating an image acquiring method that can be performed by the endoscope system 1 with the above configuration. The imaging element 254 is a CMOS image sensor as described above, and an electronic focal-plane shutter is employed. Therefore, when a plurality of frames are sequentially captured, accumulated charges are read for each horizontal line. Consequently, a time lag occurs between a horizontal line that is read first by the imaging element 254 and a horizontal line that is read last. In Embodiment 1, the time lag is approximately equal to one frame Tf.

In the example illustrated in FIG. 4, the imaging element 254 sequentially reads pixels, starting from a horizontal line in the upper portion of a screen and continuing to horizontal lines in the lower portion. In addition, the light source device 6 switches between different types of illumination lights with a cycle of the one frame period Tf. As an example of the different types of illumination lights, white illumination is employed as one type of illumination and NBI illumination is employed as the other type of illumination. In this case, the exposure period for one frame of the sensor 254a corresponds to a period including a timing at which the illumination intensity is switched.

In an exposure period P1 illustrated in FIG. 4, horizontal lines in the upper portion of the screen are dominantly exposed under first illumination emitted in a first illumination period L1, and horizontal lines in the lower portion of the screen are dominantly exposed under second illumination emitted in a second illumination period L2. Therefore, image data 101 based on pixel information read by the reading unit 254g in a transfer period T1 for charges accumulated according to light received by the light-receiving unit 254f in the exposure period P1 is image data in which the upper portion and the lower portion are subjected to different types of illumination and images captured under two different types of illumination are mixed.

By contrast, in an exposure period P2 illustrated in FIG. 4, horizontal lines in the upper portion of the screen are dominantly exposed under second illumination, and horizontal lines in the lower portion of the screen are dominantly exposed under the first illumination. Therefore, image data 102 based on pixel information read by the reading unit 254g in a transfer period T2 for charges accumulated according to light received by the light-receiving unit 254f in the exposure period P2 is image data in which images captured under two different types of illumination are mixed, similarly to the image data 101.

In Embodiment 1, it is possible to generate image data in which images captured under two different types of illumination are not mixed even when an image is captured by switching a plurality of types of illumination by using the CMOS-type imaging element 254. This will be explained in detail below.

Figure 5:
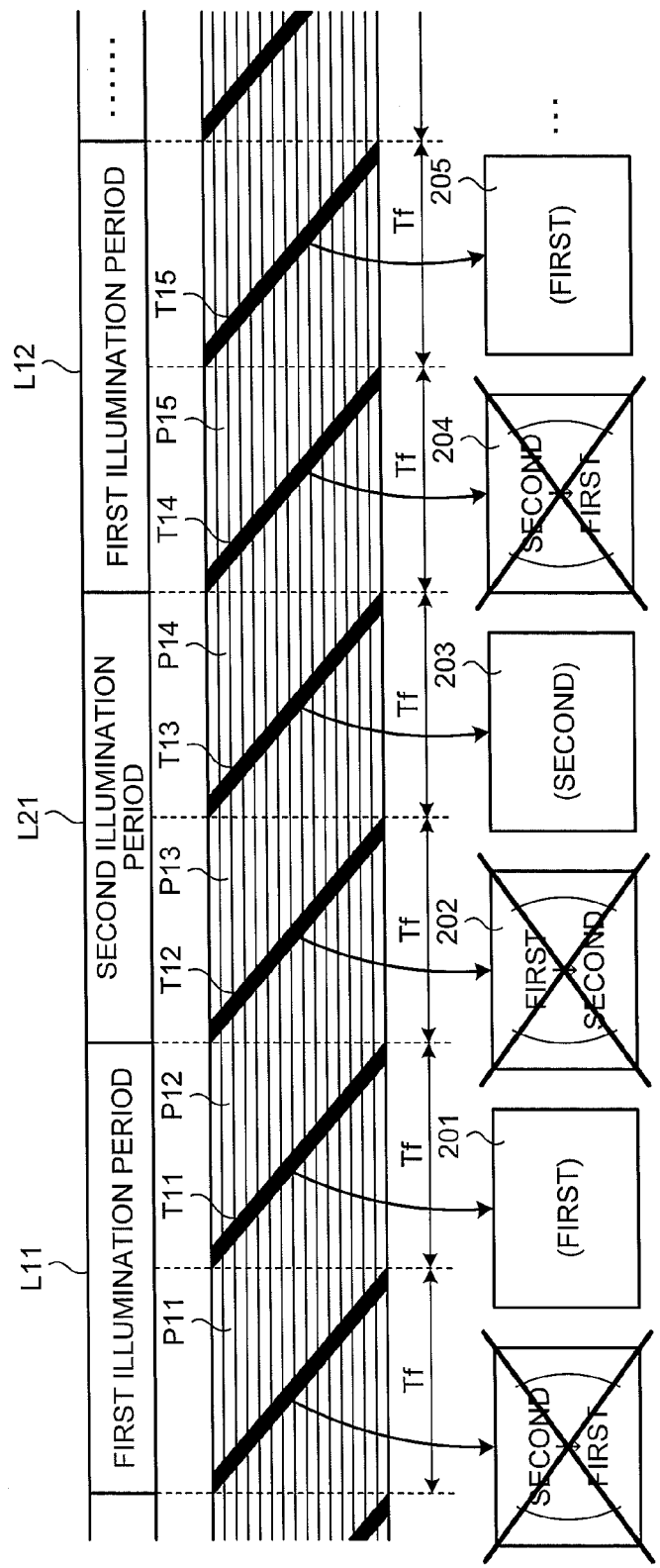
FIG. 5 is a diagram schematically illustrating an overview of an image acquiring method distinctive to the endoscope system according to Embodiment 1 of the present invention.

FIG. 5 is a diagram schematically illustrating an overview of an image acquiring method distinctive to the endoscope system 1. In the example illustrated in FIG. 5, the control device 4 of the endoscope system 1 switches illumination at an interval of two frame periods, and acquires only illumination in the second frame as image data. More specifically, the control unit 49 of the control device 4 performs controlling to acquire image data corresponding to pixel information read by the sensor 254a during a period of the second frame of the two frame periods, while on the other hand, not to acquire image data corresponding to pixel information read by the sensor 254a during a period of the first frame of the two frame periods. Here, instead of not acquiring the image data corresponding to the pixel information read by the sensor 254a during the period of the first frame, the control unit 49 may perform controlling to acquire all pieces of image data corresponding to all pieces of pixel information read by the sensor 254a, then to eliminate image data corresponding to pixel information during the period of the first frame from a processing target of the image processor 42.

In FIG. 5, an exposure period P11 contained in a first illumination period L11 includes only exposure under the first illumination. Therefore, the control device 4 acquires image data 201 which is based on pixel information corresponding to light received by the light-receiving unit 254f during the exposure period P11 and read out by the reading unit 254g at a transfer period T11 for transferring charges accumulated during the exposure period P11. On the other hand, the control device 4 does not acquire image data 202 which is based on pixel information corresponding to light received by the light-receiving unit 254f during the exposure period P12 across the first illumination period L11 and the second illumination period L21 and read out by the reading unit 254g at a transfer period T12 for transferring charges accumulated during the exposure period P12.

Subsequently, the control device 4 acquires image data 203 which is based on pixel information corresponding to light received by the light-receiving unit 254f during the exposure period P13 contained in the second illumination period L21 and read out by the reading unit 254g at a transfer period T13 for transferring charges accumulated by the light-receiving unit 254f during the exposure period P13. On the other hand, the control device 4 does not acquire image data 204 which is based on pixel information corresponding to light received by the light-receiving unit 254f during the exposure period P14 across the second illumination period L21 and the first illumination period L12 and read out by the reading unit 254g at a transfer period T14 for transferring charges accumulated by the light-receiving unit 254f during the exposure period P14.

Thereafter, the control device 4 acquires image data 205 which is based on pixel information corresponding to light received by the light-receiving unit 254f during the exposure period P15 contained in the first illumination period L12 and read out by the reading unit 254g at a transfer period T15 for transferring chages accumulated during the exposure period P15.

In this way, the control device 4 acquires only image data which is based on pixel information exposed by a single type of illumination from among pieces of the pixel information read by the reading unit 254g. Therefore, the problem with the focal-plane electronic shutter as described above can be relieved.

According to Embodiment 1 of the present invention as explained above, a plurality of types of illumination lights are sequentially emitted by each illumination period having a length corresponding to at least two frame periods and defined in accordance with each illumination light. Here, the period in which the sensor reads pixel information of one screen is one unit frame period. Then, image data corresponding to pixel information read by the sensor in the last one frame period of the illumination period is acquired, while on the other hand, image data corresponding to pixel information read by the sensor in the first one frame period of the illumination period is not acquired. Therefore, it becomes possible to acquire only image data captured under a single type of illumination light. Consequently, even when a CMOS-type imaging element is used, it is possible to capture an image at approximately the same timing while ensuring adequate sensitivity under a plurality of types of illumination that are switched periodically.

Furthermore, according to Embodiment 1, it is sufficient for the control device to select whether to acquire an image according to switched illumination light of the light source device. Therefore, it is not necessary to change the way to read pixel information at the tip portion of the endoscope, basic operations, such as setting of image reception and an output timing of operation clock signal, or the like. Consequently, it is possible to realize a seamless operation even when a plurality of types of illumination light is switched.

Modification 1-1

Figure 6:
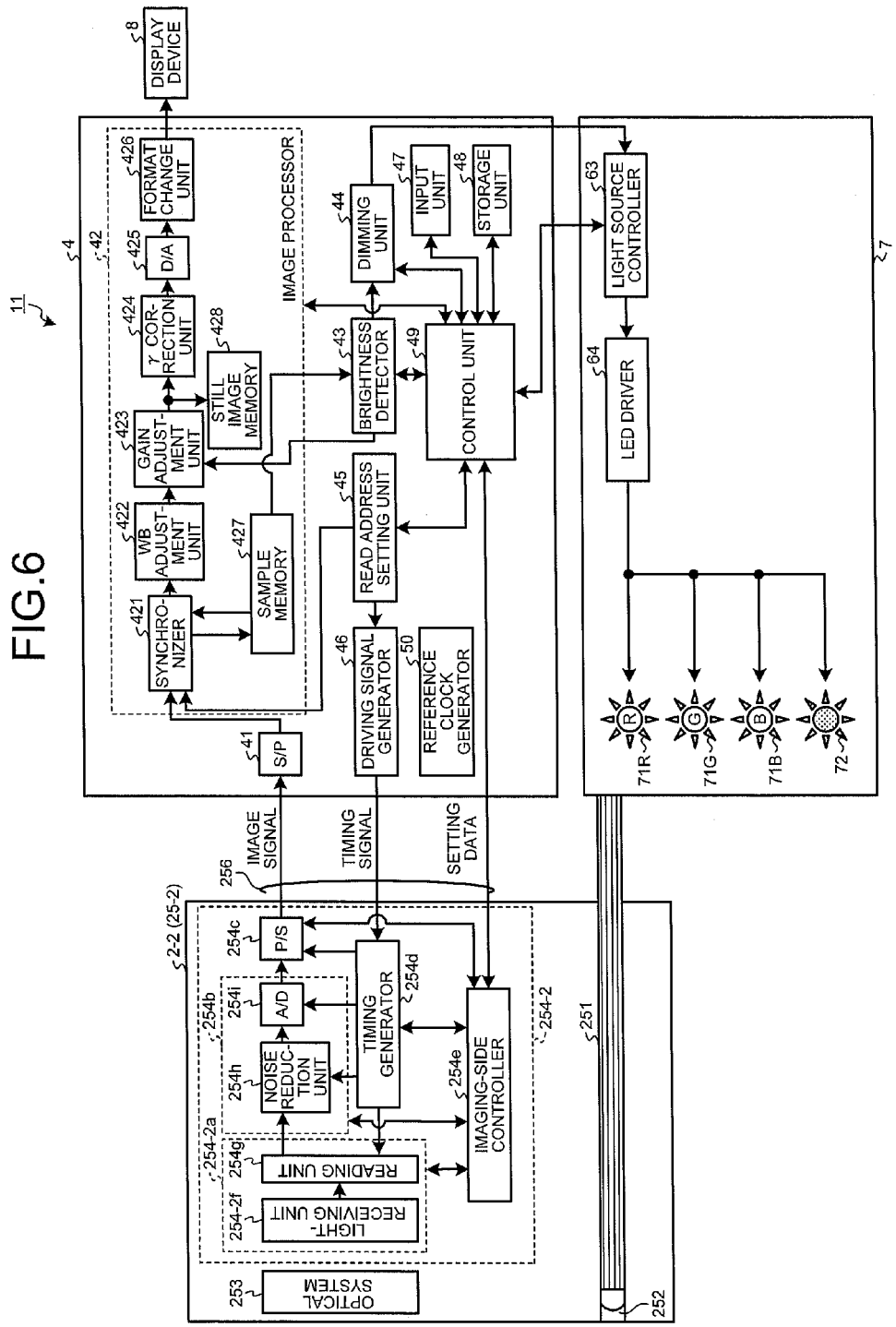
FIG. 6 is a diagram illustrating a schematic configuration of an endoscope system serving as an imaging apparatus according to Modification 1-1 of Embodiment 1 of the present invention.

FIG. 6 is a block diagram illustrating a functional configuration of a main part of an endoscope system according to Modification 1-1 of Embodiment 1 of the present invention. An endoscope system 11 illustrated in FIG. 6 includes an endoscope 2-2, the control device 4, a light source device 7, and the display device 8.

In the endoscope 2-2, a color filter is not provided in a light-receiving unit 254-2f of an imaging element 254-2. A configuration of the endoscope 2-2 other than the above is the same as the configuration of the endoscope 2 described above.

The light source device 7 includes a red light source 71R including a red LED, a green light source 71G including a green LED, a blue light source 71B including a blue LED, a special light source 72, the light source controller 63, and the LED driver 64. The light source device 7 has a function to radiate illumination light based on the frame sequential method using illumination light of three colors of red (R), green (G), and blue (B). Here, the red light is light in the wavelength band of about 610 to 780 nm, the green light is light in the wavelength band of about 500 to 570 nm, and the blue light is light in the wavelength band of about 400 to 500 nm. When radiating white light, the light source device 7 turns on all of the red light source 71R, the green light source 71G, and the blue light source 71B to form the white light. The light source device based on the frame sequential method may be configured such that a plurality of types of illumination light are switched by rotating a disc-shaped rotary filter provided with color filters for R, G, and B in front of the white light source of the light source device 7.

Figure 7:
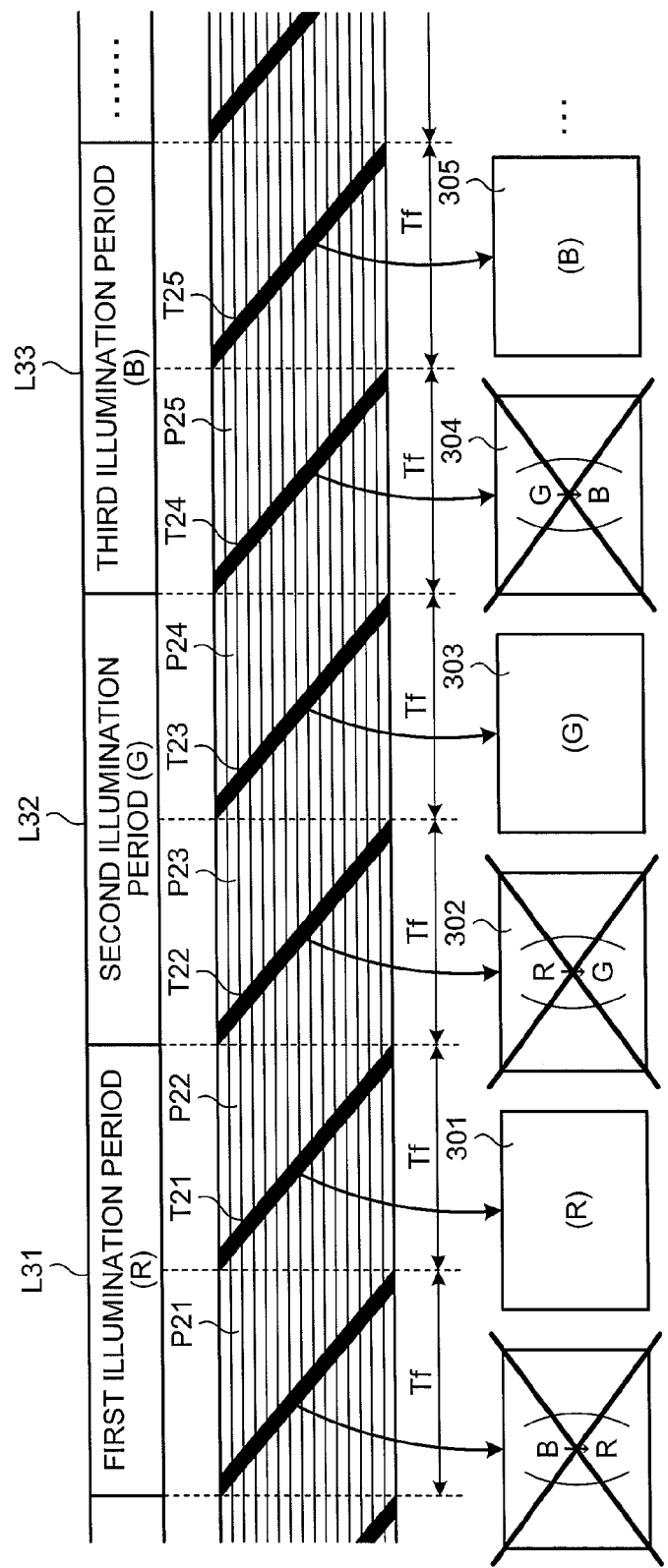
FIG. 7 is a diagram schematically illustrating an overview of an image acquiring method characteristic for the endoscope system serving as the imaging apparatus according to Modification 1-1 of Embodiment 1 of the present invention.

FIG. 7 is a diagram schematically illustrating an overview of an image acquiring method characteristic for the endoscope system 11. In the example illustrated in FIG. 7, the light source device 7 sequentially radiates red (first illumination), green (second illumination), and blue (third illumination) in this order for two frame periods for each light. The control device 4 acquires image data based on pixel information in the second frame within each illumination period. Specifically, the control device 4 acquires image data 301 which is based on pixel information corresponding to light received by the light-receiving unit 254-2f during an exposure period P21 from the first frame to the second frame of the first illumination period L31 and read out by the reading unit 254g at the transfer period T21. Further, the control device 4 acquires image data 303 which is based on pixel information corresponding to light received by the light-receiving unit 254-2f during the exposure period P23 from the first frame to the second frame of the second illumination period L32 and read out by the reading unit 254g at the transfer period T23 for transferring charges accumulated during the exposure period P23. Still further, the control device 4 acquires image data 305 which is based on pixel information corresponding to light received by the light-receiving unit 254-2f during the exposure period P25 from the first frame to the second frame of the third illumination period L33 and read out by the reading unit 254g at the transfer period T25 for transferring charges accumulated during the exposure period P25.

On the other hand, the control device 4 does not acquire image data 302 which is based on pixel information corresponding to light received by the light-receiving unit 254-2f during an exposure period P22 across different illumination periods (the first illumination period L31 and the second illumination period L32) and read out by the reading unit 254g at the transfer period T22 for transferring charges accumulated during the exposure period P22. Further, the control device 4 dose not acquire image data 304 which is based on pixel information corresponding to light received by the light-receiving unit 254-2f during an exposure period P24 across different illumination periods (the second illumination period L32 and the third illumination period L33) and read out by the reading unit 254g at the transfer period T24 for transferring charges accumulated during the exposure period P24.

According to Modification 1-1 of Embodiment 1 as explained above, it is possible to provide an endoscope system that can cope with illumination light of the frame sequential method and that can achieve the same advantageous effects as those of Embodiment 1.

As described above, Embodiment 1 can be applied to a system in which a plurality of types of illumination lights are switched for every two frames.

Embodiment 2

Figure 8:
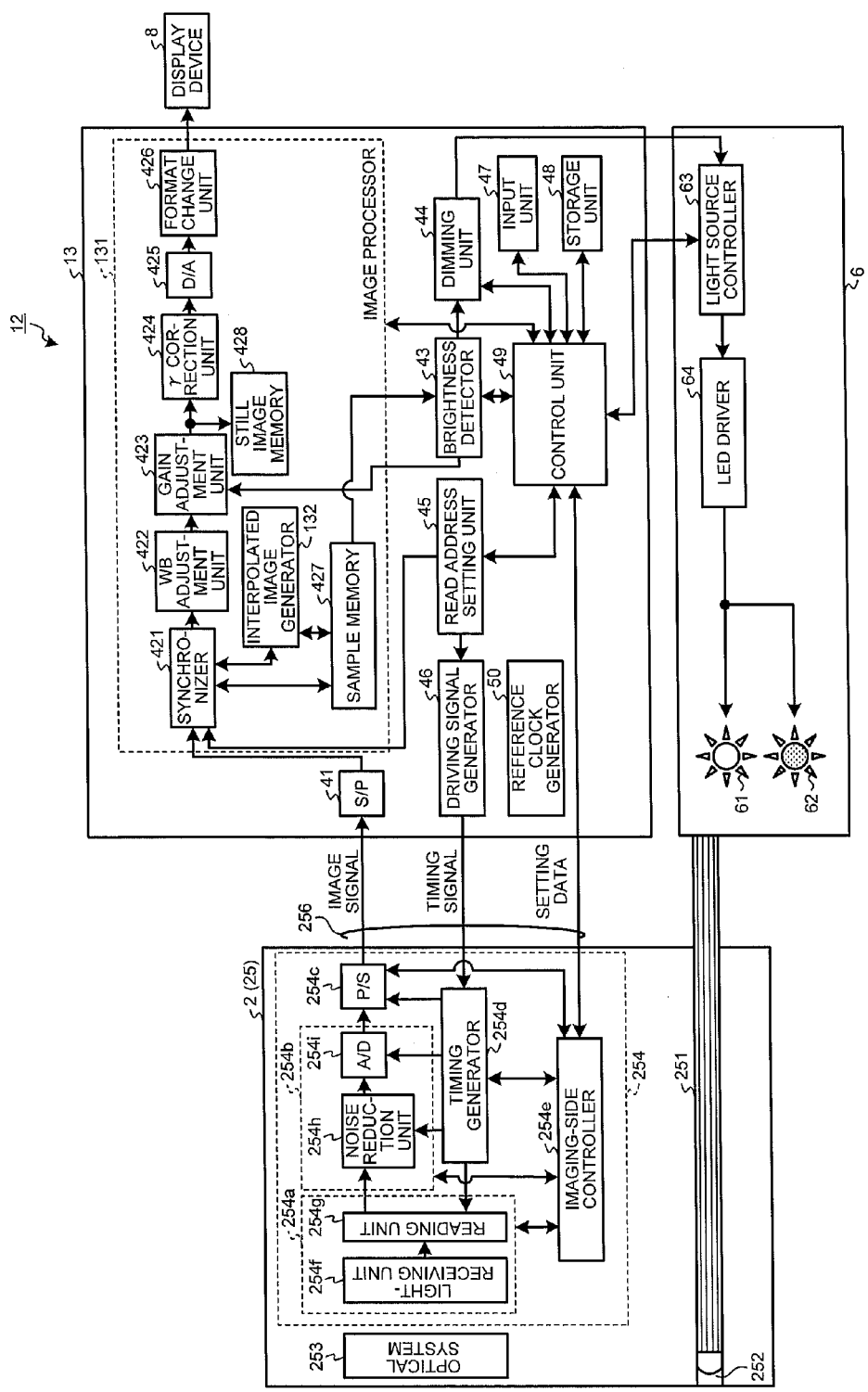
FIG. 8 is a block diagram illustrating a functional configuration of a main part of an endoscope system according to Embodiment 2 of the present invention.

FIG. 8 is a block diagram illustrating a functional configuration of a main part of an endoscope system serving as an imaging apparatus according to Embodiment 2 of the present invention. An endoscope system 12 illustrated in FIG. 8 includes the endoscope 2, a control device 13, the light source device 6, and the display device 8.

In the control device 13, a configuration of an image processor differs from the control device 4 of the endoscope system 1 described above. An image processor 131 of the control device 13 includes an interpolated image generator 132 that generates interpolated image data for interpolation between two pieces of image data that are captured under a single type of illumination and that are acquired by the control device 13 at consecutive times, in addition to the configuration of the image processor 42 of the control device 4.

Figure 9:
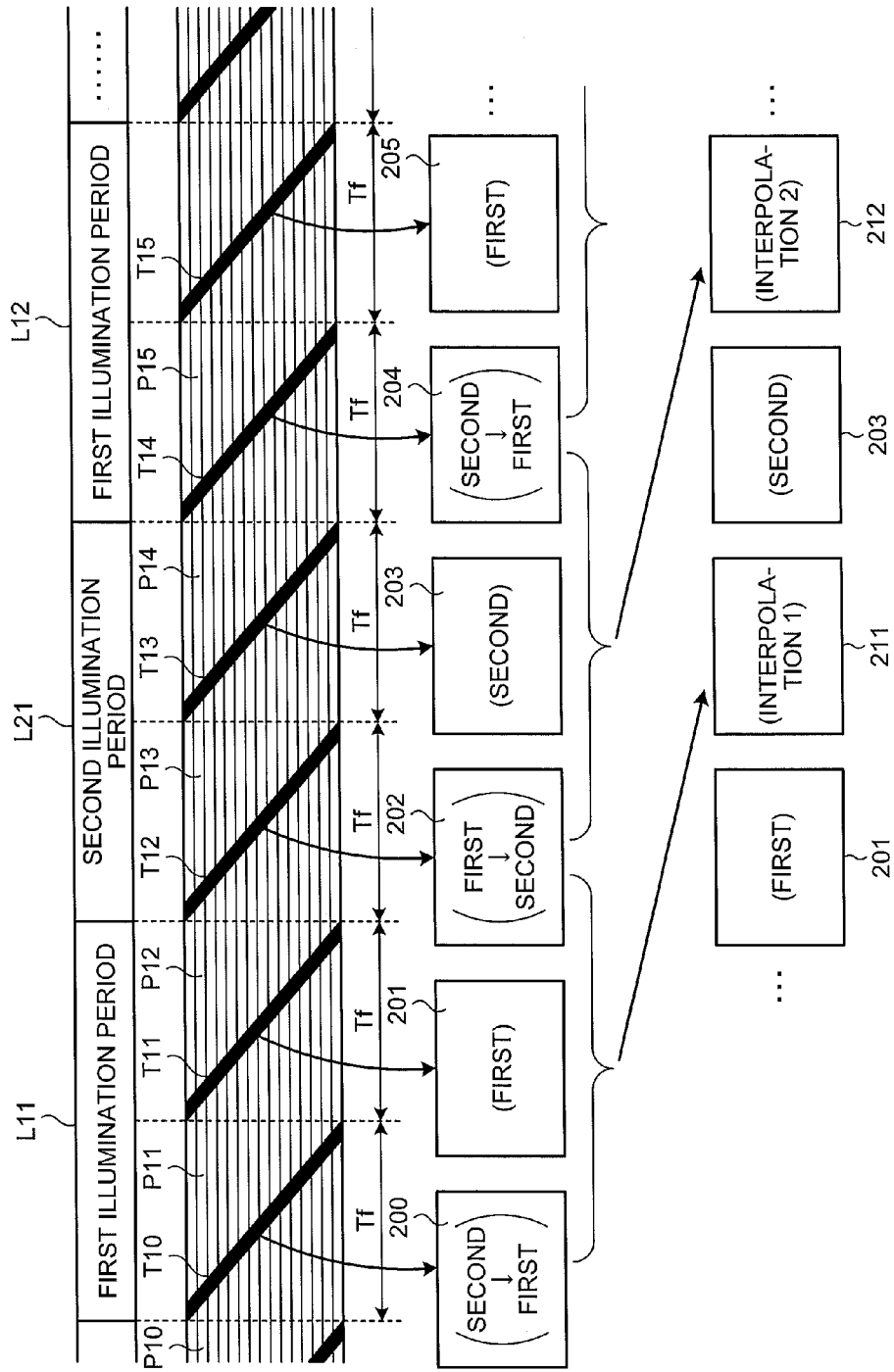
FIG. 9 is a diagram schematically illustrating an overview of an image acquiring method distinctive to the endoscope system according to Embodiment 2 of the present invention.

FIG. 9 is a diagram schematically illustrating an overview of an image acquiring method distinctive to the endoscope system 12. In FIG. 9, a relationship among the illumination period, the exposure period, and the transfer period is the same as illustrated in FIG. 5. In Embodiment 2, the control device 13 acquires the image data 201 and the image data 203 that are captured under a single type of illumination, and the interpolated image generator 132 generates interpolated image data 211 for interpolation between the image data 201 and the image data 203. Furthermore, the interpolated image generator 132 generates interpolated image data 212 for interpolation between the image data 203 and the image data 205 after the image data 203 is generated. Therefore, the control device 13 alternately outputs the pieces of the image data 201, 203, 205, . . . acquired from the endoscope 2 and the pieces of the interpolated image data 211, 212, . . . generated by the interpolated image generator 132 to the display device 8.

A method for generating the interpolated image data by the interpolated image generator 132 will be explained in detail below. The interpolated image generator 132 generates interpolated image data by using three pieces of image data 200, 201, and 202 that are sequentially read by the reading unit 254g. In this case, the image data 201 in the intermediate frame among the three sequential pieces of the image data is image data corresponding to pixel information that is read according to light received under a single type of illumination (the first illumination). The interpolated image generator 132 reads the image data 200 and the image data 201 from the sample memory 427, reads the image data 202 from the synchronizer 421, and calculates pixel values of mutually-corresponding pixels according to Equation (1) below, to thereby generate the interpolated image data 211.

(Interpolated image data 211)=(Image data 200)+(Image data 202)−(Image data 201)   (1)

Subsequently, the interpolated image generator 132 reads the image data 202 and the image data 203 from the sample memory 427, reads the image data 204 from the synchronizer 421, and calculates pixel values of mutually-corresponding pixels according to Equation (2) below, to thereby generate the interpolated image data 212.

(Interpolated image data 212)=(Image data 202)+(Image data 204)−(Image data 203)   (2)

In this case, the image data 203 in the intermediate frame among the three pieces of the image data corresponds to pixel information that is read according to light received under a single type of illumination (the second illumination).

Subsequently, the interpolated image generator 132 sequentially generates interpolated images by repeating the above processes.

According to Embodiment 2 of the present invention as explained above, it is possible to achieve the same advantageous effects as those of Embodiment 1. In addition, according to Embodiment 2, the interpolated image data is generated by using image data in a frame in which a plurality of types of illumination are mixed. Therefore, it is possible to ensure the brightness and continuity of a moving image because of using all captured frames, enabling to obtain a smoother image.

Modification 2-1

Figure 10:
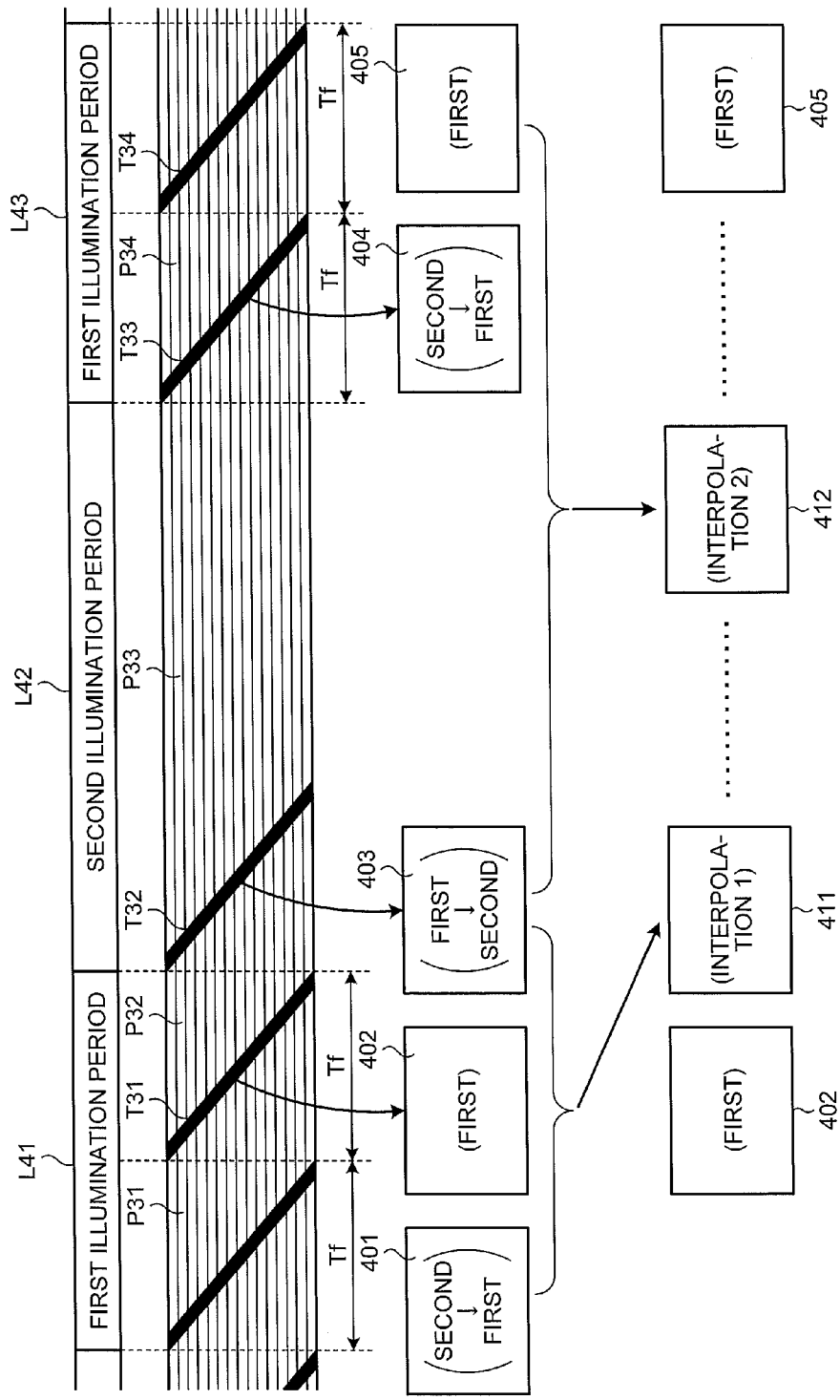
FIG. 10 is a diagram schematically illustrating an overview of an image acquiring method characteristic for an endoscope system according to Modification 2-1 of Embodiment 2 of the present invention.

FIG. 10 is a diagram schematically illustrating an overview of an image acquiring method distinctive to an endoscope system according to Modification 2-1 of Embodiment 2. In Modification 2-1, it is possible to set a non-uniform frame rate for an image to be acquired, by causing the light-receiving unit 254f to perform exposure while one of two types of alternately-radiated illumination lights is applied for an increased period. Such a situation occurs when, for example, a still image is captured while a moving image is being captured or when an irradiation period is changed due to input from any of the switches 30.

In the example illustrated in FIG. 10, the interpolated image generator 132 generates two pieces of interpolated image data between image data 402 and image data 405. Here, the image data 402 is based on pixel information corresponding to light received by the light-receiving unit 254f during an exposure period P31 under a single type of illumination in a first illumination period L41 and read out by the reading unit 254g at a transfer period T31 for transferring charges accumulated by the light-receiving unit 254f during the exposure period P31. Further, the image data 405 is based on pixel information corresponding to light received by the light-receiving unit 254f during an exposure period P34 under a single type of illumination in a first illumination period L43 and read out by the reading unit 254g at a transfer period T34 for transferring charges accumulated by the light-receiving unit 254f during the exposure period P34.

Of the two pieces of the interpolated image data generated by the interpolated image generator 132, pixel values of pixels of interpolated image data 411 that is generated after the image data 402 are obtained by Equation (3) below by using image data 401 and image data 403 that are obtained before and after the image data 402.

(Interpolated image data 411)=(Image data 401)+(Image data 403)−(Image data 402)   (3)

On the other hand, interpolated image data 412 generated by the interpolated image generator 132 after the interpolated image data 411 is obtained by Equation (4) below by using the image data 403, image data 404 and image data 405. Here, the image data 403 is based on pixel information read by the reading unit 254g at a transfer period T32 that is a sole transfer period within a second illumination period L42. Further, the image data 404 is based on pixel information read by the reading unit 254g at a first transfer period T33 (corresponding to an increased exposure period P33) within the subsequent first illumination period L43. Still further, the image data 405 is based on pixel information read in the subsequent transfer period T34 (corresponding to the exposure period P34 under a single type of illumination).

(Interpolated image data 412)=(Image data 403)+(Image data 404)−(Image data 405)   (4)

In FIG. 10, the image data 402, the pieces of the interpolated image data 411 and 412, and the image data 405 that are output to the display device 8 are arranged independent of the illumination periods and read timings. Namely, it is noted that the interpolated image data 412 and the image data 405 are generated after the pixel information is read at the transfer period T34.

According to Modification 2-1 of Embodiment 2 explained above, even when a non-uniform frame rate is set by increasing the exposure time under a single type of illumination, it is possible to achieve the same advantageous effects as those of Embodiment 2 by generating an interpolated image.

Modification 2-1 of Embodiment 2 is useful for a case where, for example, a still image is acquired while a normal moving image is captured and an exposure time for the still image varies.

Embodiment 3

Embodiment 3 of the present invention provides an image acquiring method that can cope with a case where images are captured at different sensitivities by switching illumination. A configuration of an endoscope system according to Embodiment 3 is the same as the configuration of the endoscope system 1 explained in Embodiment 1.

FIG. 11 is a diagram schematically illustrating an overview of an image acquiring method characteristic for the endoscope system 1 according to Embodiment 3. In the example illustrated in FIG. 11, the first illumination is special light and the second illumination is white light illumination. In this case, it is necessary to capture an image at higher sensitivity under the first illumination. In FIG. 11, illumination is switched to a second illumination period L52 of two frames between first illumination periods L51 and L53. Such a situation where imaging is intermittently switched to white light imaging while special light imaging is performed is caused to occur when structure information of an observed region is acquired by the white light imaging and a location of a lesion site is specified.

When the illumination light is switched, at least one frame period is needed for the switching because a gain setting for imaging or an operation mode is changed. Therefore, in Embodiment 3, one frame just after the illumination is switched is used as a period for the switching, and the control device 4 is caused to acquire pixel information read in a subsequent frame.

Details of the processes performed by the endoscope system 1 will be explained below with reference to FIG. 11. When the light source device 6 switches from illumination by the special light source 62 to illumination by the white light source 61, the control device 4 does not acquire image data 503 that is based on pixel information read by the reading unit 254*g* at a first transfer period T42 (corresponding to an exposure period P42 across the first illumination period L51 and the second illumination period L52). Similarly, when the light source device 6 switches from illumination by the white light source 61 to illumination by the special light source 62, the control device 4 does not acquire image data 505 that is based on pixel information read by the reading unit 254*g* in a first transfer period T44 (corresponding to an exposure period P44 across the second illumination period L52 and the first illumination period L53).

According to Embodiment 3 of the present invention as explained above, it is possible to achieve the same advantageous effects as those of Embodiment 1 as described above.

Meanwhile, in Embodiment 3, it may be possible to perform interpolation on a frame corresponding to the period for a switching process by using image data just before the frame (image data 502 or image data 504 in FIG. 11). Consequently, it becomes possible to reduce flicker that occurs on the display screen when the display device 8 displays data.

Modification 3-1

Modification 3-1 of current Embodiment 3 has a feature in that it performs an illumination-light switching operation when a freeze signal for freezing an image is input by a freeze switch provided as one of the switches 30 of the endoscope 2, and it stores images acquired with special light and white light before and after receiving input from the switch.

FIG. 12 is a diagram schematically illustrating an overview of an image acquiring method distinctive to an endoscope system according to Modification 3-1 of Embodiment 3. In FIG. 12, the image acquiring method is the same as that of Embodiment 3 as described above. In Modification 3-1 of Embodiment 3, when the freeze switch is turned on, the light source device 6 switches the light source to enter the second illumination period L52 after exposure of any of the horizontal lines of the light-receiving unit 254*f* being exposed at this time (at the time of switch-on in FIG. 12) is finished.

After a lapse of a predetermined time (two frame periods in the example in FIG. 12) since entrance to the second illumination period L52, the light source device 6 switches the illumination light source again to enter the first illumination period L53. The control device 4 collectively records and stores, in the storage unit 48, the image data 502 that is based on pixel information read by the reading unit 254*g* at a transfer period T41 just before the first switching of the illumination and the image data 504 that is based on pixel information read by the reading unit 254*g* at a transfer period T43 corresponding to an exposure period P43 under a single type of illumination of the second illumination period L52.

According to Modification 3-1 of Embodiment 3 as explained above, even when a freeze process is performed, it is possible to capture and store two pieces of image data under two different types of illumination at approximately the same timing without changing imaging timings.

Other Embodiments

While the embodiments of the present invention have been explained above, the present invention is not limited to the first to the third embodiments described above. For example, the present invention may be applied to a system that switches between intensities of the same type of illumination, instead of switching between different types of illumination.

Furthermore, in the present invention, the order of reading the pixel information by the reading unit is not limited to the order starting from the horizontal line in the upper portion of a screen. The order of reading may be changed appropriately.

Moreover, in the present invention, when the same type of illumination light is continuously radiated, the control device may acquire all pieces of image data based on all pieces of pixel information read by the sensor.

As described above, the present invention may include various embodiments not described herein, and various design changes and the like may be performed within the technical ideas described in the appended claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
    a light source unit that is capable of emitting a plurality of types of illumination lights;
    a sensor in which a plurality of pixels that each generates, upon receipt of light, an electrical signal through photoelectric conversion are arranged on a two-dimensional plane, wherein
        the sensor is capable of reading, as pixel information, electrical signals generated by pixels arbitrary designated as a read target area from among the pixels, and is capable of sequentially reading a plurality of horizontal lines on a line-by-line basis;
    a control unit that performs controlling to read the pixel information from the pixels belonging to the read target area by each frame, wherein
        one frame period is a period from when an exposure period for exposing the pixels on a horizontal line that is to be read first from among the horizontal lines belonging to the read target area of the sensor is started and until when reading of the pixel information generated by each of the pixels on the horizontal line is completed;
    a light source controller that controls the light source unit to sequentially emit, by each illumination period of a length corresponding to at least two frame periods, the illumination lights in synchronization with start of the exposure period of the horizontal line that is to be read first from the sensor,
    an interpolated image generator that generates interpolated image data for interpolation between two pieces of image data acquired at consecutive times among image data acquired by the control unit, by using pixel information which is based on light received by the sensor during a period including a timing at which the illumination lights are switched;
    wherein the control unit performs the predetermined controlling by performing controlling to exclude, from a predetermined processing target, image data corresponding to the pixel information read by the sensor during a first frame period of the illumination period among the pixel information read by the sensor in each frame, while on the other hand by acquiring image data corresponding to the pixel information read by the sensor during other frame period of the illumination period among the pixel information read by the sensor in each frame.

2. The imaging apparatus according to claim 1, wherein the control unit performs controlling not to acquire image data corresponding to the pixel information read by the sensor during the first frame period of the illumination period.

3. The imaging apparatus according to claim 1, wherein
the length of the illumination period determined in accordance with each of the types of the illumination lights corresponds to two frame periods, and
the interpolated image generator generates the interpolated image data by using image data acquired during a last frame period of the illumination period and by using pixel information on two screens read by the sensor during frame periods before and after a period in which the image data is acquired.

4. The imaging apparatus according to claim 1, wherein the lengths of the illumination periods determined based on the respective types of the illumination lights are the same.

5. The imaging apparatus according to claim 1, wherein
the light source unit emits, as the illumination light, white light and light with spectral characteristics different from the white light, and
the light source controller causes the light source unit to intermittently emit the white light while sequentially emitting special light in a specific wavelength band.

* * * * *